(12) United States Patent
Craig et al.

(10) Patent No.: US 7,456,000 B2
(45) Date of Patent: Nov. 25, 2008

(54) DEACTIVATION OF LINKING MOIETIES IN ANTIBODY-ENZYME CONJUGATES

(75) Inventors: Alan R. Craig, Wilmington, DE (US); Steve Kramer, Middletown, DE (US); Ashok Koul, Wilmington, DE (US)

(73) Assignee: Siemens Healthcare Diagnostics Inc., Deerfield, IL (US)

( * ) Notice: Subject to any disclaimer, the term of this patent is extended or adjusted under 35 U.S.C. 154(b) by 265 days.

(21) Appl. No.: 11/198,535

(22) Filed: Aug. 5, 2005

(65) Prior Publication Data

US 2006/0046290 A1    Mar. 2, 2006

Related U.S. Application Data

(60) Provisional application No. 60/605,106, filed on Aug. 26, 2004.

(51) Int. Cl.
*C07K 1/00* (2006.01)
*C07K 14/00* (2006.01)

(52) U.S. Cl. .................. 435/188.5; 530/350; 530/391.1

(58) Field of Classification Search .................. None
See application file for complete search history.

(56) References Cited

U.S. PATENT DOCUMENTS

| | | | |
|---|---|---|---|
| 3,966,556 A | 6/1976 | Rubenstein et al. | 435/188 |
| 4,053,590 A | 10/1977 | Bonsen et al. | 424/177 |
| 4,190,496 A | 2/1980 | Rubenstein et al. | 435/7 |
| 4,203,802 A | 5/1980 | Rubenstein et al. | 435/188 |
| 4,218,539 A | 8/1980 | Weltman | 435/188 |
| 4,248,969 A | 2/1981 | Lee | 435/176 |
| 4,250,260 A | 2/1981 | Rohrbach et al. | 435/176 |
| 4,278,651 A | 7/1981 | Hales | 424/1 |
| 4,423,143 A | 12/1983 | Rubenstein et al. | 435/7 |
| 4,657,853 A | 4/1987 | Freytag et al. | 435/7 |
| 4,994,385 A | 2/1991 | Bieniarz et al. | 435/177 |
| 5,053,520 A | 10/1991 | Bieniarz et al. | 548/520 |
| 5,066,789 A * | 11/1991 | Srinivasan et al. | 530/391.5 |
| 5,164,311 A * | 11/1992 | Gupta | 435/188 |
| 5,241,078 A | 8/1993 | Moreland et al. | 548/542 |
| 5,324,650 A | 6/1994 | Obzansky et al. | 435/188 |
| 5,412,083 A | 5/1995 | Giese et al. | 536/20 |
| 5,651,971 A | 7/1997 | Lees | 424/194.1 |
| 2002/0058804 A1 | 5/2002 | Barbas, III et al. | 536/53 |
| 2002/0068329 A1 | 6/2002 | Gehrmann et al. | 435/69.7 |
| 2004/0018974 A1 | 1/2004 | Arbogast et al. | 514/12 |

OTHER PUBLICATIONS

Melton et al. (Advanced Drug Delivery Reviews 1996; 22: 289-301).*
Melton, Roger G., "Preparation and Purification of Antibody-Enzyme Conjugates for Therapeutic Applications", Advanced Drug Delivery Reviews 1996; 22, pp. 289-301.

* cited by examiner

*Primary Examiner*—Brandon J Fetterolf
(74) *Attorney, Agent, or Firm*—Theodore J. Leitereg

(57) ABSTRACT

In some embodiments, the present invention pertains to a method for conjugating a first compound to a second compound wherein the conjugation involves an electrophilic moiety. The method comprises reacting the first compound with the second compound to form a conjugate. The improvement in embodiments of the present invention comprises adding a nucleophilic reagent to the conjugate wherein the nucleophilic reagent forms a neutral product upon reaction with unreacted electrophilic moieties of the conjugate. In some embodiments, the nucleophilic reagent is substantially non-reactive with disulfide bonds in the event that the conjugate comprises disulfide bonds. The conjugate formed is doubly deactivated because the other moiety for linking to the electrophilic moiety is also deactivated.

23 Claims, No Drawings

DEACTIVATION OF LINKING MOIETIES IN ANTIBODY-ENZYME CONJUGATES

CROSS-REFERENCE TO RELATED APPLICATIONS

This application claims the benefit of the subject matter disclosed in prior Provisional Patent Application Ser. No. 60/605,106 filed Aug. 26, 2004, the disclosure of which is incorporated herein by reference in its entirety.

BACKGROUND OF THE INVENTION

In the fields of medicine and clinical chemistry, many studies and determinations of physiologically reactive species such as cells, proteins, enzymes, cofactors, nucleic acids, substrates, antigens, antibodies, and so forth are carried out using conjugates involving specific binding pair members or labels or the like. Various assay techniques that involve the binding of specific binding pair members are known. These assay techniques generally also involve a label used in the detection part of the assay.

The use of enzyme labels for the determination of analytes in immunoassays has shown substantial promise and numerous immunoassays have been developed, which are dependent upon the accurate measurement of enzymatic activity from an assay medium.

Numerous enzyme immunoassay methods are known for the determination of the presence in a sample of an analyte. The assays include both homogeneous and heterogeneous assays. Some homogeneous approaches comprise determining the effect that the sample containing the analyte has on the binding between a conjugate of the analyte (ligand) and an enzyme and a receptor for the analyte. When the conjugate and the receptor bind, a modulation of the enzymatic activity occurs. The presence of analyte in the sample can be determined from the effect that the analyte has on the modulation of the enzymatic activity when compared to that obtained in the absence of analyte or in the presence of known amounts of analyte. Heterogeneous assays include sandwich format assays. The aforementioned assays are discussed in more detail below.

Polypeptides can be conjugated with enzymes using preactivated enzymes such as, for example, enzymes preactivated with a maleimide or a haloacetyl moiety. The polypeptides may comprise free sulfhydryl (—SH) groups or may be treated to introduce such groups. In the latter circumstance, linking groups may be employed to link to the polypeptide to introduce sulfhydryl groups. Accordingly, the linking group may have an amine-reactive functionality in addition to the sulfhydryl group where the amine reactive functionality reacts with free amine groups on the polypeptide. Maleimide-activated enzyme is reacted with free sulfhydryl (—SH) groups present in, or introduced into, the polypeptide to form a stable thiol ether linkage.

In another approach, amino groups of a polypeptide are acylated with a heterobifunctional crosslinking agent such as N-succinimidyl 4'-(p-maleimidophenyl) butyrate. This crosslinking agent has a N-hydroxysuccinimide group at one end of the molecule that reacts with amino groups. The maleimide moiety at the other end of the heterobifunctional agent reacts with free sulfhydryl groups of a polypeptide.

In the above reactions, it is standard practice to terminate the conjugation reaction with a quench reagent that deactivates one of the reactive groups that is used to form the conjugate, namely, free sulfhydryl groups remaining on the product after the conjugation reaction has taken place. The sulfhydryl groups are deactivated by adding a reagent reactive with the sulfhydryl groups such as, for example, a sulfhydryl receptor, e.g., a maleimide, and so forth.

There remains a need for methods for producing ligand binder-polypeptide conjugates such as, for example, enzyme-polypeptide conjugates, polynucleotide-polypeptide conjugates, and so forth, that exhibit good stability, activity, sensitivity, and the like.

SUMMARY

In some embodiments, the present invention pertains to a method for conjugating a first compound to a second compound wherein the conjugation involves an electrophilic moiety. The method comprises reacting the first compound with the second compound to form a conjugate. The improvement in embodiments of the present invention comprises adding a nucleophilic reagent to the conjugate wherein the nucleophilic reagent forms a neutral product upon reaction with unreacted electrophilic moieties of the conjugate. In some embodiments, the nucleophilic reagent is substantially non-reactive with disulfide bonds in the event that the conjugate comprises disulfide bonds.

In some embodiments, the present invention is directed to a method for conjugating a first polypeptide to a second polypeptide wherein the conjugation involves a sulfhydryl receptor. The first polypeptide is combined with the second polypeptide under conditions for the first polypeptide and the second polypeptide to react to form a conjugate involving the sulfhydryl receptor. Then, a sulfhydryl receptor deactivation reagent is added to the conjugate and the sulfhydryl receptor deactivation reagent forms a neutral deactivated product upon reaction with the sulfhydryl receptor.

In some embodiments, the present invention is directed to a conjugate comprising a first polypeptide and a second polypeptide linked together by sulfhydryl groups bound to sulfhydryl receptors. The sulfhydryl receptors that are not bound to sulfhydryl groups are in the form of a neutral product of the reaction of a sulfhydryl receptor and a sulfhydryl receptor deactivation reagent. In some embodiments, the sulfhydryl receptor deactivation reagent is substantially non-reactive with disulfide linkages when the conjugate comprises disulfide bonds.

DESCRIPTION OF SPECIFIC EMBODIMENTS

The present invention provides a simple, inexpensive method for conjugation of macromolecules together to form conjugates that are useful in assays such as, for example, immunoassays. Typically, as explained above, the conjugation process involves two different reactive groups or moieties. For the most part, the known techniques have focused on deactivation of only one of the two residual reactive groups. The conjugates of the invention have deactivated residual reactive groups for both of the reactive moieties that are used to form the conjugates.

As mentioned above, in some embodiments, the present invention pertains to a method for conjugating a first compound to a second compound wherein the conjugation involves at least one reactive moiety that is an electrophilic moiety. The method comprises reacting the first compound with the second compound to form a conjugate. The improvement in embodiments of the present invention comprises adding a nucleophilic reagent to the conjugate subsequent to the conjugation reaction wherein the nucleophilic reagent forms a neutral product upon reaction with unreacted or residual electrophilic moieties of the conjugate. In some embodiments, the nucleophilic reagent is substantially non-reactive with disulfide bonds, which might be present in one or both of the two compounds that are conjugated together. Furthermore, a reactive moiety used in the conjugation with the reactive electrophilic moiety may be, and in many embodiments is, deactivated also with a suitable deactivation reagent thereby yielding a di-deactivated conjugate.

Conjugates

The first compound and the second compound are usually macromolecules, usually two different macromolecules including ligand receptors. A ligand is any organic compound for which a receptor naturally exists or can be prepared and the ligand receptor is the receptor for such ligand.

The term "macromolecule" or "ligand receptor" includes biopolymers such as, for example, polynucleotides, polypeptides, polysaccharides, and the like, which generally have a molecular weight of at least about 5,000, more usually at least about 10,000. A biopolymer is a polymer of one or more types of repeating units or monomers. Biopolymers are typically found in biological systems. In the polypeptide, polysaccharide or polynucleotide category, the molecules are generally from about 5,000 to about 50,000,000 or more molecular weight, or from about 10,000 to about 30,000,000 or more molecular weight, or about 20,000 to about 10,000,000 molecular weight or more. Polypeptides are compounds or compositions that are poly(amino acids), that is, polymeric amino acids and are sometimes referred to as proteins. Polynucleotides are compounds or compositions that are polymeric nucleotides or nucleic acid polymers. Polysaccharides are compounds or compositions that are polymeric carbohydrates.

The above terms also include analogs of the monomeric parts such as, for example, those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions.

A wide variety of proteins are included within the term "polypeptide." Such proteins include proteins having particular biological functions, proteins related to specific microorganisms, particularly disease causing microorganisms, etc. Exemplary of such proteins are immunoglobulins or antibodies, cytokines, enzymes, hormones, cancer antigens, nutritional markers, tissue specific antigens, avidin, streptavidin, folate binding proteins, hormone receptors, protein A, protein G, and so forth. Polynucleotides include single-stranded or double-stranded DNA, RNA, modified DNA, modified RNA, m-RNA, r-RNA, t-RNA, cDNA, DNA-RNA duplexes, etc.

Embodiments of the invention have application to the conjugation of many types of compounds where two or more reactive functionalities are reacted together to form the conjugate. A reactive functionality is a group or moiety that is capable of reacting with another group or moiety. Both groups or moieties, thus, are referred to as functional groups or moieties. The reactive functionality may be reactive by virtue of electrophilicity, nucleophilicity, basicity, acidity, free radical activity, photochemical activity, or the like. Such reactive functionalities include, for example, thiol or sulfhydryl, amine, carboxy, hydroxy, olefin, substituted olefin, epoxide, aldehyde, alkyl halide, and so forth.

A reactive functionality may be present on the compound to be conjugated naturally or it may be introduced by chemical reaction, by introduction using a heterobifunctional or homo-bifunctional reagent and so forth. Such chemical reactions to introduce a reactive functionality are dependent on the nature of the reactive functionality, the nature of the moiety to be reacted with, structural features of the macromolecule being modified, and the like. Such chemical reactions are apparent to those skilled in the art.

A linking group may be employed to connect two or more substructures, namely, two or more compounds. The linking group may vary from a bond to a chain of from 1 to about 30 or more atoms, from about 1 to about 20 atoms, from 1 to about 10 atoms, each independently selected from the group normally consisting of carbon, oxygen, sulfur, nitrogen, and phosphorous, usually carbon and oxygen. The number of heteroatoms in the linking group may range from about 0 to about 8, from about 1 to about 6, from about 2 to about 4. The number of atoms in the chain is determined by counting the number of atoms other than hydrogen or other monovalent atoms along the shortest route between the substructures being connected. The atoms of the linking group may be substituted with atoms other than hydrogen such as carbon, oxygen and so forth in the form, e.g., of alkyl, aryl, aralkyl, hydroxyl, alkoxy, aryloxy, aralkoxy, and the like. As a general rule, the length of a particular linking group can be selected arbitrarily to provide for convenience of synthesis with the proviso that there be minimal interference caused by the linking group with the ability of the compounds to be linked together. The linking group may be aliphatic or aromatic. Functionalities present in the linking group may include esters, thioesters, amides, thioamides, ethers, ureas, thioureas, guanidines, azo groups, thioethers, carboxylate and so forth. Examples, by way of illustration and not limitation, of various linking groups that may find use in the present invention are found in U.S. Pat. No. 3,817,837, particularly at column 30, line 69, to column 36, line 10, which disclosure is incorporated herein by reference in its entirety. The order of reacting the linking group with the compounds may involve reacting one compound with the linking group followed by reaction with the other compound. Simultaneous reaction is also possible but not preferred in most instances. The order of reaction is determined by the nature of the linking group, the nature of the reactive functionalities, the nature of the compounds to be linked, the stability of the reactive compounds and intermediates, and so forth.

Embodiments of the present invention have particular application to the conjugation of labels such as, for example, enzymes, phycobiliproteins, latex particles, radio-labeled proteins, fluorescent dye-labeled proteins, chromophore-labeled proteins, chemilumiflours, generic binding proteins such as streptavidin, and the like with macromolecules or ligand receptors such as, for example, antibodies, to prepare conjugates useful in assays such as, for example, immunoassays. Enzyme-macromolecule conjugates are typically used for the detection and determination of substances present in very low quantities, for example, picogram to nanogram quantities of substances in biological fluids, such as urine and serum. A wide variety of enzymes may be used to form the conjugate, but the enzymes selected are often those enzymes that can be detected with great sensitivity. In the preparation of enzyme conjugates, it is most desirable to produce enzyme conjugates such as enzyme antibody conjugates of high stability, high specificity and good reproducibility. The nature of the enzyme selected for the conjugate depends on the nature of the assay, the nature of the detection system, and the like.

The enzyme may be any enzyme that is suitable as a label for detection in an assay. Such enzymes include, by way of illustration and not limitation, beta-galactosidase, alkaline phosphatase, glucose-6-phosphate dehydrogenase ("G6PDH"), horseradish peroxidase, luciferases, kinases, oxidases, and so forth. Other enzymes and coenzymes, which may be linked in place of an enzyme, are disclosed in Litman, et al., U.S. Pat. No. 4,275,149, columns 19-28, and Boguslaski, et al., U.S. Pat. No. 4,318,980, columns 10-14; suitable fluorescers and chemiluminescers are disclosed in Litman, et al., U.S. Pat. No. 4,275,149, at columns 30 and 31; which are incorporated herein by reference.

The antibody as ligand receptor can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, Fab', and the like. In addition, aggregates, polymers, and conjugates of immunoglobulins or their fragments can be used where appropriate so long as binding affinity for a particular molecule is maintained.

One of the linking moieties is usually an electrophilic moiety such as, for example, a moiety comprising a sulfhydryl receptor, an aldehyde, an active ester, and the like. The electrophilic moiety may be part of a mono-functional reagent where the agent comprises only one linking moiety. On the other hand, the electrophilic moiety may be part of a bi-functional reagent, a tri-functional reagent, and so forth. Such reagents comprise one or more functionalities for linking other than the electrophilic moiety.

Examples of sulfhydryl receptors are carbonyl-substituted olefins, sulfone-substituted olefins, carbonyl substituted, halogen substituted carbon atoms, pyridyl disulfide groups, epoxides, and so forth. The carbonyl substituted olefin is generally an olefin (carbon-carbon double bond) that may be substituted with one, two, or more carbonyl groups. The carbonyl groups include, for example, carboxyl, carboxamide, carboximide, carboxylic ester, anhydride, aldehyde, ketone, and the like. One example of a carbonyl substituted olefin is a maleimide or maleimidyl moiety, which includes, by way of illustration and not limitation, N-(4-carboxycyclohexylmethyl)maleimide, N-(m-benzoyl)maleimide, m-maleimido-benzoyl-N-hydroxysulfosuccinimide ester, succinimidyl maleimidylacetate, and succinimidyl 6-maleimidylhexanoate, N-succinimidyl 4'-(p-maleimidophenyl) butyrate, meta-maleimidobenzoyl N-hydroxysuccinimide ester, N-hydroxysuccinimide ester of N-(m-benzoyl)maleimide, N-succinimidyl-4-(N-maleimidomethyl) cyclohexane-1-carboxylate (SMCC), N-maleimidobenzoyl-N-hydroxysuccinimide ester (MBS), and the like.

Examples of halogen substituted, carbonyl substituted carbon atoms include iodoacetic acid, iodoacetic anhydride, N-hydroxysuccinimide ester of iodoacetic acid, other active esters of iodoacetic acid, and the like. The sulfone-substituted olefins include compounds wherein the sulfone bond electrons are conjugated with the electrons of the olefin bond, i.e., the olefin bond is conjugated with the sulfone moiety.

Groups reactive with the sulfhydryl receptor to form the enzyme antibody conjugates include, for example, sulfhydryl, e.g., thiol or mercaptan, hydrazine derivative, hydrazide, amino-oxy ether, and the like. Sulfhydryl groups may be present naturally in the molecule to be conjugated or they may be introduced into the molecule such as by chemical reaction and the like. Methods for introducing sulfhydryl groups may be found in "Enzyme Immunoassay," by Eiji Ishikawa, (Lippincott Williams & Wilkins, July 1981.

The reaction conditions employed in the formation of the conjugate between an enzyme and an antibody where one of the molecules comprises a sulfhydryl group (either naturally or introduced) and the other of the molecules comprises a sulfhydryl receptor (either naturally or introduced) usually involves bringing a reaction mixture comprising the above to a pH in the range of about 5-10, more usually in the range of about 6-9. Various buffers may be used such as phosphate, carbonate, Tris, and the like. An aqueous solvent is normally used and up to about 40 weight % of an oxyethylene alcohol or ether having from 1 to 3 oxyethylene units may be present. The temperatures normally range from about −5° C. to about 40° C., usually from about 0° C. to about 25° C. Conditions for the reaction are usually determined by the nature of the antibody and/or the enzyme, the nature of the linking moieties and so forth.

Deactivation of Linking Moieties in Conjugates

As mentioned above, in the above reactions, it is standard practice to terminate the conjugation reaction with a quench reagent that deactivates one of the reactive groups that is used to form the conjugate, namely, free sulfhydryl groups remaining on the product after the conjugation reaction has taken place. The free sulfhydryl groups are deactivated by adding a reagent reactive with the sulfhydryl groups such as, for example, a sulfhydryl receptor, e.g., a maleimide (N-ethyl maleimide and other maleimides discussed above), reagents comprising sulfhydryl receptors other than maleimide as discussed above, and so forth.

We have found that, in addition to deactivation of nucleophilic moieties such as remaining sulfhydryl groups, it is advantageous to deactivate free electrophilic moieties such as sulfhydryl receptors remaining on the product after conjugation thereby yielding a di-deactivated conjugate. This is counter-intuitive because one might reasonably conclude that deactivating one of the reactive groups would thereby substantially reduce or eliminate any reactions that might occur between the free groups. Furthermore, an enhancement in specific activity of the conjugates is realized as explained more fully below.

In some embodiments of the invention, a nucleophilic reagent is added to the conjugate subsequent to formation wherein the nucleophilic reagent forms a neutral product upon reaction with unreacted electrophilic moieties of the conjugate. The term "neutral product" means that the resulting deactivated moiety is free of a positive or negative charge such as might be found with a carboxylic acid functionality, amine functionality, and so forth, resulting from the reaction of the nucleophilic moiety with the electrophilic moiety of the conjugate. In some embodiments the neutral product results from the formation of a ring structure or cyclized product upon reaction of the deactivation reagent with the electrophilic moiety. Consequently, in some embodiments the nucleophilic reagent is one that results in the formation of a stable ring structure or cyclized product upon reaction of the nucleophilic reagent with free electrophilic moieties remaining in the conjugate. In some embodiments, the deactivation reagent or nucleophilic reagent is substantially non-reactive with disulfide bonds in the event that the conjugate comprises disulfide bonds. By "substantially non-reactive" is meant that reaction with disulfide bonds does not occur to an extent that the activity of the moiety comprising the disulfide bonds is changed to any appreciable extent such that its effectiveness is compromised.

The deactivated product should exhibit good activity and stability. A desirable goal for stability is that there must be less than a 5% and in some embodiments less than a 4%, less than a 3%, less than a 2% change in response over one month for product stored at 4° C. Response is defined as recovered analyte, which is generally proportional to the response of the assay. For example, if the assay response is a change in optical density due to enzymatic activity with a chromogenic substrate, the response seen in the assay will be measured in absorbance units. In the above example, the assay response in absorbance units should change by less than 5% over one month in order to obtain the desired goal for stability.

Deactivation reagents for deactivating the electrophilic moiety, for example, a sulfhydryl receptor, include compounds of the following formula:

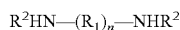

wherein n is 0 or 1, $R^1$ is alkylene or substituted alkylene and $R^2$ is independently H, alkyl or substituted alkyl. When n is 0, there is a direct bond between the nitrogen atoms. Alkylene means a branched or unbranched saturated divalent hydrocarbon radical. In some embodiments alkylene includes, for example, alkylene of 1 to about 5 carbon atoms, alkylene of 1 to about 4 carbon atoms, alkylene of 1 to about 3 carbon atoms, alkylene of 1 to 2 carbon atoms, alkylene of about 2 to about 5 carbon atoms, alkylene of about 2 to about 4 carbon atoms, alkylene of about 2 to about 3 carbon atoms, alkylene of about 3 to about 5 carbon atoms, alkylene of about 3 to about 4 carbon atoms, alkylene of about 4 to about 5 carbon atoms. Particular examples include methylene, ethylene, propylene, 2-methylpropylene, 1,2-dimethylpropylene, butylene, pentylene, and the like.

Alkyl means a monovalent branched or unbranched radical derived from an aliphatic hydrocarbon by removal of one H atom; includes both lower alkyl and upper alkyl.

Lower alkyl means alkyl containing from 1 to 5 carbon atoms, from 1 to about 4 carbon atoms, from 1 to about 3 carbon atoms, from 1 to 2 carbon atoms, from about 2 to about 5 carbon atoms, from about 2 to about 4 carbon atoms, from about 2 to about 3 carbon atoms, from about 3 to about 5 carbon atoms, from about 3 to about 4 carbon atoms, from about 4 to about 5 carbon atoms, such as, e.g., methyl, ethyl, propyl, butyl, isopropyl, isobutyl, pentyl, isopentyl, etc.

Upper alkyl means alkyl containing more than about 6 carbon atoms, usually about 6 to about 30 carbon atoms, about 10 to about 20 carbon atoms, about 6 to about 25 carbon atoms, about 6 to about 20 carbon atoms, about 10 to about 15 carbon atoms, such as, e.g., hexyl, heptyl, octyl, etc.

Substituted means that a hydrogen atom of a molecule has been replaced by another atom, which may be a single atom or part of a group of atoms forming a functionality as described above. Such substituents include by way of illustration and not limitation alkyl, and so forth.

In some embodiments the above deactivation reagents are desirable because they are not reactive with disulfide bonds where the conjugate comprises a component that contains disulfide bonds such as, for example, where the conjugate comprises an antibody. In some embodiments the deactivation agent for electrophilic moieties includes, for example, hydrazine, alkylene diamines of 1 to 5 carbon atoms such as, for example, methylene diamine (diaminomethane), ethylene diamine (1,2-diaminoethane), propylene diamine (1,3-diaminopropane), and so forth, substituted hydrazines such as, for example, alkyl (lower alkyl and upper alkyl) substituted hydrazine, substituted diamines such as, for example, alkyl (lower alkyl and upper alkyl) substituted diamines, and the like.

Mercaptans are also useful as deactivation reagents for electrophilic moieties in some embodiments of the invention where a member or component of the conjugate does not comprise disulfide bonds. The mercaptans are desirably free of amino groups. For embodiments where a member of the conjugate contains disulfides, it is desirable to employ mercaptans that do not reduce the disulfides. Examples of suitable mercaptans include, by way of illustration and not limitation, thiophenol, and other thiols that have less reducing potential than the thiols generated when biological disulfides are cleaved, and so forth. Thiols that are strong reducing agents and, therefore, could cleave the disulfides that maintain the tertiary structure of polypeptides of the conjugate are undesirable because they destroy the activity of these polypeptides.

The amount of the nucleophilic deactivation reagent to be added to deactivate residual sulfhydryl receptors of the conjugate depends on the nature of the electrophilic moiety and the nucleophilic deactivation reagent, the nature of the components of the conjugate such as, for example, the number of expected free electrophilic moieties in the conjugate product, the rate of reaction, and so forth. Usually, the amount of the nucleophilic deactivation reagent added is in excess of the expected amount needed so that substantially all of the free electrophilic moieties are deactivated. The amount is usually determined empirically and is the amount sufficient to deactivate the free electrophilic moieties of the conjugate to obtain a conjugate exhibiting enhanced activity.

The reaction conditions employed to deactivate the residual sulfhydryl receptors are dependent on the nature of the deactivation reagent, the nature of the sulfhydryl receptor, the chemical reactivity of the components of the conjugate, and so forth. For the most, particular reaction conditions will be evident to those skilled in the art without undue experimentation based on the disclosure herein and information available in the art. Usually, an aqueous medium is employed, which may comprise one or more organic solvents such as alcohols, ethers, amides, sulfoxides, sulfones, esters, and the like in a percentage range of about 1% to about 50% or more. The temperature employed for the deactivation reaction may be, for example, about 0° C. to about 100° C., about 5° C. to about 50° C., about 10° C. to about 40° C., about 15° C. to about 30° C. The deactivation reaction is carried out for a time period sufficient for reactions to occur. Usually, the deactivation is carried out, for example, for a period of about 1 hour to about 48 hours.

Use of Deactivated Conjuqates

The di-deactivated conjugates of the present invention can be utilized in many known assays for analytes. The assay methods usually involve a sample suspected of containing an analyte, which is combined in an assay medium with reagents for carrying out the assay. Such reagents can include a binding partner for the analyte such as, e.g., an antibody for the analyte, analyte analogs, solid surfaces to which one of the above reagents is bound, binding partners for sbp members, and so forth. One or more of the reagents can be labeled with a label such as, e.g., an enzyme. The reagents are chosen such that a signal is obtained from a label in relation to the presence or amount of analyte in the sample. The assay can be performed either without separation (homogeneous) or with separation (heterogeneous) of any of the assay compounds or products.

Homogeneous immunoassays are exemplified by the EMIT® assay products (Syva Company, San Jose, Calif.) disclosed in Rubenstein, et al., U.S. Pat. No. 3,817,837, column 3, line 6 to column 6, line 64; enzyme channeling techniques such as those disclosed in Maggio, et al., U.S. Pat. No. 4,233,402, column 6, line 25 to column 9, line 63; and other enzyme immunoassays such as the enzyme linked immunosorbant assay ("ELISA") are discussed in Maggio, E. T., infra. The above disclosures are all incorporated herein by reference.

Heterogeneous assays usually involve one or more separation steps and can be competitive or non-competitive. A variety of competitive and non-competitive heterogeneous assay formats are disclosed in Davalian, et al., U.S. Pat. No. 5,089,390, column 14, line 25 to column 15, line 9, incorporated herein by reference. In a typical competitive heterogeneous assay a support having an antibody for analyte bound thereto is contacted with a medium containing the sample and analyte analog conjugated to a detectable label such as an enzyme conjugate. Analyte in the sample competes with the conjugate for binding to the antibody. After separating the support and the medium, the label activity of the support or the medium is determined by conventional techniques and is related to the amount of analyte in the sample.

A typical non-competitive sandwich assay is an assay disclosed in David, et al., U.S. Pat. No. 4,486,530, column 8, line 6 to column 15, line 63, incorporated herein by reference. In this method, an immune sandwich complex is formed in an assay medium. The complex comprises the analyte, a first antibody (monoclonal or polyclonal) that binds to the analyte and a second antibody that binds to the analyte or a complex of the analyte and the first antibody. Subsequently, the immune sandwich complex is detected and is related to the amount of analyte in the sample. The immune sandwich complex is detected by virtue of the presence in the complex of a label wherein either or both the first antibody and the second antibody contain labels or substituents capable of combining with labels.

Sandwich assays find use for the most part in the detection of antigen and receptor analytes. In the assay two antibodies specific for the analyte bind the analyte and, thus, the assay is also referred to as the two-site immunometric assay. In one approach a first incubation of unlabeled antibody coupled to a support, otherwise known as the insolubilized antibody, is contacted with a medium containing a sample suspected of containing the analyte. After a wash and separation step, the support is contacted with a medium containing the second antibody, which generally contains a label, for a second incubation period. The support is again washed and separated from the medium and either the medium or the support is examined for the presence of label. The presence and amount of label is related to the presence or amount of the analyte. For a more detailed discussion of this approach see U.S. Pat. Nos. Re 29,169 and 4,474,878, the relevant disclosures of which are incorporated herein by reference.

In a variation of the above sandwich assay, the sample in a suitable medium is contacted with labeled antibody for the analyte and incubated for a period of time. Then, the medium is contacted with a support to which is bound a second antibody for the analyte. After an incubation period, the support is separated from the medium and washed to remove unbound reagents. The support or the medium is examined for the presence of the label, which is related to the presence or amount of analyte. For a more detailed discussion of this approach see U.S. Pat. No. 4,098,876, the relevant disclosure of which is incorporated herein by reference.

In another variation of the above, the sample, the first antibody bound to a support and the labeled antibody are combined in a medium and incubated in a single incubation step. Separation, wash steps and examination for label are as described above. For a more detailed discussion of this approach see U.S. Pat. No. 4,244,940, the relevant disclosure of which is incorporated herein by reference.

Detection of antibodies is a useful tool in the diagnosis of infectious diseases. Detection of autoantibodies is also useful in the diagnosis of autoimmune disease. Some of the above assay methods can be used to detect numerous antibodies such as antibodies to human immunodeficiency virus ("HIV"), rubella or herpes and autoantibodies such as autoantibodies to insulin, to glutamic acid decarboxylase ("GAD"), both the 65 kd and the 67 kd isoforms but more particularly, $GAD_{65}$; and to other islet cell antigens.

The following provides a description of some of the terms used above with respect to the described assays.

Member of a specific binding pair ("sbp member") means one of two different molecules, having an area on the surface or in a cavity, which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs such as biotin-avidin, hormones-hormone receptors, nucleic acid duplexes, IgG-protein A, polynucleotide pairs such as DNA-DNA, DNA-RNA, and the like are not immunological pairs but are included in the definition of sbp member for the purpose of describing this invention.

Analyte means the compound or composition to be detected. The analyte can be comprised of a member of a specific binding pair (sbp) and may be a ligand, which is usually monovalent, usually haptenic, or a ligand receptor, which is usually polyvalent, and is a single compound or plurality of compounds that share at least one common epitopic or determinant site.

The monovalent ligand analytes will generally be from about 100 to 2,000 molecular weight, more usually, from 125 to 1,000 molecular weight. The analytes include drugs, metabolites, pesticides, pollutants, and the like. Representative analytes, by way of example and not limitation, include (i) alkaloids such as morphine alkaloids, which include morphine, codeine, heroin, dextromethorphan, their derivatives and metabolites; cocaine alkaloids, which include cocaine and benzyl ecgonine, their derivatives and metabolites; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; diterpene alkaloids, their derivatives and metabolites; (ii) steroids, which include the estrogens, androgens, andreocortical steroids, bile acids, cardiotonic glycosides and aglycones, which includes digoxin and digoxigenin, saponins and sapogenins, their derivatives and metabolites; steroid mimetic substances, such as diethylstilbestrol; (iii) lactams having from 5 to 6 annular members, which include the barbiturates, e.g., Phenobarbital and secobarbital, diphenylhydantoin, primidone, ethosuximide, and their metabolites; (iv) aminoalkylbenzenes, with alkyl of from 2 to 3 carbon atoms, which include the amphetamines; catecholamines, which include ephedrine, L-dopa, epinephrine; narceine; papaverine; and metabolites of the above; (v) benzheterocyclics which include oxazepam, chlorpromazine, tegretol, their derivatives and metabolites, the heterocyclic rings being azepines, diazepines and phenothiazines; (vi) purines, which includes theophylline, caffeine, their metabolites and derivatives; (vii) drugs derived from marijuana, which include cannabinol and tetrahydrocannabinol; (viii) hormones such as thyroxine, cortisol, triiodothyronine, testosterone, estradiol, estrone, progesterone, polypeptides such as angiotensin, LHRH, and immunosuppressants such as cyclosporin, FK506, mycophenolic acid (MPA), and so forth; (ix) vitamins such as A, B, e.g. B12, C, D, E and K, folic acid, thiamine; (x) prostaglandins, which differ by the degree and sites of hydroxylation and unsaturation; (xi) tricyclic antidepressants, which include imipramine, dismethylimipramine, amitriptyline, nortriptyline, protriptyline, trimipramine, chlomipramine, doxepine, and desmethyldoxepin; (xii) antineoplastics, which include methotrexate; (xiii) antibiotics, which include penicillin, chloromycetin, actinomycetin, tetracycline, terramycin, the metabolites and derivatives; (xiv) nucleosides and nucleotides, which include ATP, NAD, FMN, adenosine, guanosine, thymidine, and cytidine with their appropriate sugar and phosphate substituents; (xv) miscellaneous individual drugs which include methadone, meprobamate, serotonin, meperidine, lidocaine, procainamide, acetylprocainamide, propranolol, griseofulvin, valproic acid, butyrophenones, antihistamines, chloramphenicol, anticholinergic drugs, such as atropine, their metabolites and derivatives; (xvi) metabolites related to diseased states include spermine, galactose, phenylpyruvic acid, and porphyrin Type 1; (xvii) aminoglycosides, such as gentamicin, kanamicin, tobramycin, and amikacin; and (xviii) pesticides such as polyhalogenated biphenyls, phosphate esters, thiophosphates, carbamates, polyhalogenated sulfenamides, their metabolites and derivatives.

Polyvalent analytes are normally poly(amino acids), i.e., polypeptides and proteins, polysaccharides, nucleic acids, and combinations thereof. Such combinations include components of bacteria, viruses, chromosomes, genes, mitochondria, nuclei, cell membranes and the like. For the most part, the polyvalent ligand analytes will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

A wide variety of proteins may be considered as to the family of proteins having similar structural features, proteins having particular biological functions, proteins related to specific microorganisms, particularly disease causing microorganisms, etc. Such proteins include, for example, immunoglobulins, cytokines, enzymes, hormones, cancer antigens, nutritional markers, tissue specific antigens, etc. Such proteins include, by way of illustration and not limitation, protamines, histones, albumins, globulins, scleroproteins, phosphoproteins, mucoproteins, chromoproteins, lipoproteins, nucleoproteins, glycoproteins, T-cell receptors, proteoglycans, HLA, unclassified proteins, e.g., somatotropin, prolactin, insulin, pepsin, proteins found in human plasma, blood clotting factors, protein hormones such as, e.g., follicle-stimulating hormone, luteinizing hormone, luteotropin, prolactin, chorionic gonadotropin, tissue hormones, cytokines, cancer antigens such as, e.g., PSA, CEA, a-fetoprotein, acid phosphatase, CA19.9 and CA125, tissue specific antigens, such as, e.g., alkaline phosphatase, myoglobin, CPK-MB and calcitonin, and peptide hormones. Other polymeric materials of interest are mucopolysaccharides and polysaccharides.

For receptor analytes, the molecular weights will generally range from 10,000 to $2 \times 10^8$, more usually from 10,000 to $10^6$. For immunoglobulins, IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, DNA, RNA, thyroxine binding globulin, thyroxine binding prealbumin, transcortin, etc.

The term analyte further includes oligonucleotide and polynucleotide analytes such as m-RNA, r-RNA, t-RNA, DNA, DNA-RNA duplexes, etc.

The analyte may be a molecule found directly in a sample such as biological tissue, including body fluids, from a host. The sample can be examined directly or may be pretreated to render the analyte more readily detectable by removing unwanted materials. The sample may be pretreated to separate or lyse cells; precipitate, hydrolyse or denature proteins; hydrolyze lipids; solubilize the analyte; or the like. Such pretreatment may include, without limitation: centrifugation; treatment of the sample with an organic solvent, for example, an alcohol, such as methanol; and treatment with detergents. The sample can be prepared in any convenient medium, which does not interfere with an assay. An aqueous medium is preferred.

The analyte of interest may be determined by detecting an agent probative of the analyte of interest such as a specific binding pair member complementary to the analyte of interest, whose presence will be detected only when the analyte of interest is present in a sample. Thus, the agent probative of the analyte becomes the analyte that is detected in an assay.

The biological tissue includes excised tissue from an organ or other body part of a host and body fluids, for example, urine, whole blood, plasma, serum, saliva, semen, stool, sputum, cerebral spinal fluid, tears, mucus, and the like. Preferably, the sample is plasma or serum.

Hapten means a compound capable of binding specifically to corresponding antibodies, but does not itself act as an immunogen (or antigen) for preparation of the antibodies. Antibodies which recognize a hapten can be prepared against compounds comprised of the hapten linked to an immunogenic (or antigenic) carrier. Haptens are a subset of ligands.

Ligand analog means a modified ligand, an organic radical or analyte analog, usually of a molecular weight greater than 100, which can compete with the analogous ligand for a receptor, the modification providing means to join a ligand analog to another molecule. The ligand analog will usually differ from the ligand by more than replacement of a hydrogen with a bond which links the ligand analog to a hub or label, but need not. The ligand analog can bind to the receptor in a manner similar to the ligand. The analog could be, for example, an antibody directed against the idiotype of an antibody to the ligand.

Specific binding means the specific recognition of one of two different molecules for the other compared to substantially less recognition of other molecules. Generally, the molecules have areas on their surfaces or in cavities, also referred to as "binding sites," giving rise to specific recognition between the two molecules. Exemplary of specific binding are antibody-antigen interactions, enzyme-substrate interactions, polynucleotide interactions, and so forth.

Non-specific binding means non-covalent binding between molecules that is relatively independent of specific surface structures. Non-specific binding may result from several factors including hydrophobic interactions between molecules.

Support or surface means a solid phase, typically a support or surface, which is a porous or non-porous water insoluble material that can have any one of a number of shapes, such as strip, rod, plate, well, particle or bead. A wide variety of suitable supports are disclosed in Ullman, et al., U.S. Pat. No. 5,185,243, columns 10-11, Kurn, et al., U.S. Pat. No. 4,868, 104, column 6, lines 21-42, and Milburn, et al., U.S. Pat. No. 4,959,303, column 6, lines 14-31, which are incorporated herein by reference.

The surface can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed.

Binding of sbp members to a support or surface may be accomplished by well-known techniques, commonly available in the literature. See, for example, "Immobilized Enzymes," Ichiro Chibata, Halsted Press, New York (1978) and Cuatrecasas, *J. Biol. Chem.*, 245:3059 (1970).

Signal producing system ("sps") means one or more components, at least one component being a detectable label such as, e.g., an enzyme, which generate a detectable signal that relates to the amount of bound and/or unbound label, i.e. the amount of label bound or not bound to the compound being detected. Thus, the signal is detected and/or measured by detecting enzyme activity, luminescence, radioactivity, or the like, as the case may be.

There are numerous methods by which the label can produce a signal detectable by external means, desirably by visual examination, for example, by electromagnetic radiation, heat, and chemical reagents. The label or other sps members can also be bound to an sbp member, another molecule or to a support.

In some embodiments, the label may need other components to produce a signal, and the signal producing system would then include all the components required to produce a measurable signal, which may include substrates, coenzymes, enhancers, additional enzymes, substances that react with enzymic products, catalysts, activators, cofactors, inhibitors, scavengers, metal ions, dyes, fluorophores, radionucleides, and a specific binding substance required for binding of signal generating substances. A detailed discussion of suitable signal producing systems can be found in Ullman, et al., U.S. Pat. No. 5,185,243, columns 11-13, incorporated herein by reference.

The label can directly produce a signal and, therefore, additional components are not required to produce a signal. Phycobiliproteins, for example, are able to absorb light, where the light absorption transfers energy to these molecules and elevates them to an excited energy state. This absorbed energy is then dissipated by emission of light at a second wavelength.

The label and/or other sps member may be bound to an sbp member or to a support utilizing well-known procedures. Alternatively, the label can be bound covalently to an sbp member such as, for example, an antibody; a receptor for an antibody, a receptor that is capable of binding to a small molecule conjugated to an antibody, or a ligand analog. Bonding of the label to the sbp member may be accomplished by chemical reactions that result in replacing a hydrogen atom of the label with a bond to the sbp member or may include a linking group between the label and the sbp member. Other sps members may also be bound covalently to sbp members. See, for example, Rubenstein, et al., U.S. Pat. No. 3,817,837, incorporated herein by reference.

Assay means a method for the determination of the presence or amount of an analyte.

Measuring the amount of an analyte means quantitative, semiquantitative, and qualitative methods as well as all other methods for determining an analyte. For example, a method which merely detects the presence or absence of an analyte in a sample suspected of containing the analyte is considered to be included within the scope of the present invention. The terms "detecting" and "determining," as well as other common synonyms for measuring, are contemplated within the scope of the present invention.

Ancillary Materials means various materials frequently employed in the assay in accordance with the present invention. For example, buffers will normally be present in the assay medium, as well as stabilizers for the assay medium and the assay components. Frequently, in addition to these additives, proteins may be included, such as albumins; organic solvents such as formamide; quaternary ammonium salts; polyanions such as dextran sulfate; surfactants, particularly non-ionic surfactants; binding enhancers, e.g., polyalkylene glycols; or the like.

Wholly or partially sequentially refers to the combining of various agents other than concomitantly (simultaneously). One or more of the various agents may be combined with one or more of the remaining agents to form a subcombination.

The invention is demonstrated further by the following illustrative examples.

EXAMPLES

Parts and percentages herein are by weight unless otherwise indicated. Temperatures are in degrees Centigrade (° C.).

Materials:

The hCG (human chorionic gonadotropin) and CKMB (creatinine kinase, MB subtype) antibody Fab'2 fragments were prepared by a standard pepsin enzyme digestion process of mouse monoclonal antibodies that were grown in vitro. β-galactosidase was purchased from Roche Diagnostics Corporation (Roche Applied Science, Indianapolis Ind.). N-ethylmaleimide (NEM) and sulfosuccinimidyl-4-(N-maleimidomethyl)-cyclohexane-1-carboxylate (SMCC) linker were purchased from EMD Biosciences (La Jolla Calif.). All other chemicals were purchased from the Sigma-Aldrich Company (St. Louis Mo.).

Testing was done using the DIMENSION® RxL analyzer, available from Dade Behring Inc., Deerfield, Ill.

Example 1

Part A

A solution of 250 mg of anti-hCG Fab'2 antibody was prepared at a concentration of 8-10 mg/mL in 10 mM pH 7.0 phosphate buffer containing 300 mM NaCl. To this solution, 2.507 mL of a 10 mg/mL SMCC solution in DMF (dimethylformamide) was added dropwise with stirring. The mixture was then incubated for 30 minutes at 25° C., and then purified by passage through a SEPHADEX G-25® size exclusion column. The elution buffer was the same as the reaction buffer. The concentration of product was then determined using the OD280 (assuming the extinction coefficient is 1.4), and the concentration was adjusted to 2 mg/mL by addition of additional reaction buffer.

Part B.

A solution of 1350 mg of β-galactosidase in 675 mL of 10 mM pH 7.0 phosphate buffer containing 300 mM NaCl was prepared, and brought to 25° C. with stirring. When the solution had reached this temperature the solution of activated antibody from Part A above was added. The mixture was incubated at 25° C. for 2 hours and 20 minutes, and then the reaction was stopped by adding 16 mL of a 100 mM stock solution of N-ethylmaleimide (NEM) in water.

Part C.

15 minutes after addition of the NEM solution, 2 mL aliquots were removed from the product mixture. Different nucleophilic reagents, including sodium azide, sodium cyanide, thiophenol, hydrazine, and mercaptoethylamine (MEA) were added to the aliquots to give concentrations of 5, 25, and 125 mM nucleophiles. These mixtures were held for 24 hours at room temperature, and then refrigerated over night at 4° C., at which time they were filtered through 0.2 micron filters and then diluted 67-fold into the conjugate diluent used for the DIMENSION® RxL commercially available hCG conjugate reagent that is part of the hCG FLEX® kit product. The experimental reagents were then used to replace the hCG conjugate in commercially approved DIMENSION® RxL hCG FLEX® kits. These experimental kits were run using the standard software for the hCG Dimension method, using Level 4 calibrator, which contains 529 mIU hCG. The results of the testing are shown in Table 1 below:

TABLE 1

| Quench Compound | Concentration | Assay Response (mAU) | Response Change Compared to Control |
|---|---|---|---|
| Sodium Azide | 5 mM | 475 | 13% |
| | 25 mM | 528 | 26% |
| | 125 mM | 546 | 30% |
| Sodium Cyanide | 5 mM | 429 | 2% |
| | 25 mM | 371 | −12% |
| | 125 mM | 166 | −61% |
| Thiophenol | 5 mM | 546 | 30% |
| | 25 mM | 430 | 2% |
| | 125 mM | 337 | −20% |
| Hydrazine | 5 mM | 562 | 34% |
| | 25 mM | 528 | 26% |
| | 125 mM | 535 | 27% |
| Mercaptoethylamine | 5 mM | 394 | −6% |
| | 25 mM | 420 | 0% |
| | 125 mM | 439 | 4% |
| Control | No second quench | 420 | 0% |

As can be seen, the largest increase in activity was achieved with hydrazine as the nucleophilic deactivation reagent. Thiophenol also gave an adequate response.

Example 2

Part A

A solution of 500 mg of anti-CKMB Fab'2 antibody was prepared at a concentration of 8-10 mg/mL in 10 mM pH 7.0 phosphate buffer containing 300 mM NaCl. To this solution, 5.014 mL of a 10 mg/mL SMCC solution in DMF (dimethylformamide) was added dropwise with stirring. The mixture is then incubated for 30 minutes at 25° C., and then purified by passage through a SEPHADEX G-25® size exclusion column. The elution buffer was the same as the reaction buffer. The concentration of product was then determined using the OD 280 (assume the extinction coefficient is 1.4), and the concentration was adjusted to 2 mg/mL by addition of additional reaction buffer.

Part B

A solution of 2700 mg of β-galactosidase in 1350 mL of 10 mM pH 7.0 phosphate buffer containing 300 mM NaCl was prepared and brought to 25° C. with stirring. When the solution had reached this temperature the solution of activated antibody from the first step above was added. The mixture was incubated at 25° C. for 3 hours and 10 minutes, and then the reaction was stopped by adding 32 mL of a 100 mM stock solution of N-ethylmaleimide (NEM) in water.

Part C

Fifteen (15) minutes after addition of the NEM solution, 2 mL aliquots were removed from the product mixture and 0.04 mL of a 10% stock solution of TWEEN 20® was added to each aliquot. Sodium azide and hydrazine were added to two of the aliquots, and the third had no additive. The concentration of sodium azide in the first was 125 mM and the concentration of hydrazine in the second was 5 mM. The three samples were incubated for 18 hours at 20° C., and then purified by HPLC using a GF450XL® preparative column from Agilent Technologies Inc (Palo Alto Calif.). The product peak was eluted with a buffer containing 11.1 g/L monobasic sodium phosphate, 15.3 g/L dibasic sodium phosphate, and 0.2 g/L sodium azide at pH 7.0. The peak that contained higher molecular weight material than β-galactosidase was collected, and other peaks were discarded. Each of the three samples was adjusted to a concentration such that the optical density of the product at 280 nm was 1 AU.

The mixtures were filtered through 0.2 micron filters and then tested over a period of 47 days, to determine their activity and stability. Half of the conjugates was stored at 4° C., and the other half was stored at 25° C. On each test day, each experimental conjugate was diluted 16-fold with the conjugate diluent used for the DIMENSION® RxL commercially available MMB conjugate reagent that is part of the MMB FLEX® kit product. These experimental reagents were then used to replace the MMB conjugate in commercially approved DIMENSION® RxL MMB FLEX® kits. The experimental kits were tested using the standard software for the MMB DIMENSION® RxL method with a calibrator that contains 133 ng/mL of CKMB. The results of the testing are shown in Table 2 below:

TABLE 2

| Quench Condition | Storage Temperature | Response on Day 0 | Response as Percent of Day 0 | | | |
|---|---|---|---|---|---|---|
| | | | Day 5 | Day 12 | Day 19 | Day 47 |
| NEM only (control) | 4 C. | 301 | 97.5 | 95.8 | 93.8 | 88.1 |
| 5 mM Hydrazine* | 4 C. | 383 | 100.2 | 102.3 | 103.0 | 96.3 |
| 150 mM Sodium Azide* | 4 C. | 410 | 96.8 | 97.1 | 95.3 | 92.1 |
| NEM only (control) | 25 C. | 301 | 94.1 | 92.2 | 86.1 | 87.7 |
| 5 mM Hydrazine* | 25 C. | 383 | 100.5 | 96.1 | 96.0 | 88.7 |
| 150 mM Sodium Azide* | 25 C. | 410 | 92.6 | 86.5 | 84.3 | 81.9 |

*The hydrazine and azide quench examples were first quenched with NEM

As discussed above, a desirable goal for conjugate stability is that there be less than a 5% change in response over one month for product stored at 4° C. The conjugate that was quenched with both NEM and hydrazine fulfilled this criterion while the conjugate quenched with both NEM and azide did not. Accordingly, in some embodiments the nucleophilic reagent is substantially free of azide in that it contains less than about 0.1%, less than about 0.05%, less than about 0.01%, or 0%, of azide.

Example 3

In this example, conjugates were prepared at commercial scale for assays for the detection of HCG, MMB, ferritin (FERR), and cyclosporin A (CSA), respectively, on the DIMENSION® RxL following the manufacturers directions.

Part A

A solution of Fab'2 antibody (either 500 mg of anti-CKMB, 450 mg of anti-HCG, or 200 mg of anti-FERR) or intact antibody (125 mg of anti-CSA) was prepared at a concentration of 8-10 mg/mL in 10 mM pH 7.0 phosphate buffer containing 300 mM NaCl. To this solution, 30-fold molar excess of 10 mg/mL SMCC solution in DMF was added dropwise with stirring. The mixture was then incubated for 30 minutes at 25° C. and then purified by passage through a SEPHADEX G-25® size exclusion column. The elution buffer was the same as the reaction buffer. The concentration of product was then determined using the OD 280 (assuming an extinction coefficient of 1.4), and the concentration was adjusted to 2 mg/mL by addition of additional reaction buffer.

Part B

A solution of 2 mg/mL of β-galactosidase in 10 mM pH 7.0 phosphate buffer containing 300 mM NaCl was prepared and brought to 25° C. with stirring. When the solution had reached this temperature, the solution of the appropriate activated antibody from the first step above was added. The molar quantity of β-galactosidase was equal to that of the activated antibody. The mixture was incubated at 25° C. for 3 hours and 10 minutes, and then the reaction was stopped by adding a sufficient volume of a 100 mM stock solution of N-ethylmaleimide (NEM) in water to bring the final NEM concentration to 1 mM.

Part C

Fifteen (15) minutes after addition of the NEM solution, the solution was divided into 2 equal aliquots. Hydrazine was added to one aliquot, and the other had no additive. The concentration of hydrazine was 5 mM. After incubating for 15 minutes at room temperature, the aliquots were concentrated using a filter concentration unit. The concentrated aliquots were then purified using a SEPHADEX S200® column. The product peak was eluted with a buffer containing 11.1 g/L monobasic sodium phosphate, 15.3 g/L dibasic sodium phosphate, and 0.2 g/L sodium azide at pH 7.0. The peak that contained higher molecular weight material than α-galactosidase was collected, and other peaks were discarded. Each of the samples was adjusted to a concentration such that the optical density of the product at 280 nm was 1 AU. The mixtures were filtered through 0.2 micron filters and then tested for specific activity.

The specific activity of a conjugate is dependent upon both its enzymatic (β-Galactosidase) and immunologic (antibody binding) activity. For a conjugate with a given amount of enzymatic activity per molecule, the specific activity increases as the percent of Enzymatic Activity Bound to Active Antibody increases. Active antibody is defined as antibody capable of binding the antigen of interest (sbp member). An increase of a conjugate's specific activity allows less of the conjugate to be used per test on a clinical chemistry analyzer such as, for example, the Dimension® RxL, when, e.g., a non-competitive format such as a sandwich immunoassay is used.

For sandwich immunoassays such as the HCG, MMB, and FERR methods on the DIMENSION® RxL, the percentage of Enzymatic Activity Bound to Active Antibody is determined using the following procedure.

a. Prepare goat anti-mouse coated chrome particles (Pierce product # 21354, MAGNABIND™ Goat anti-Mouse IgG Beads) according to the manufacturer's instructions.

b. Hydrate method-specific chrome tablets in diluent (specific to each method) at 3 times the normal concentration (i.e., 3× the concentration after hydration in a FLEX® well).

c. Prepare an antigen solution (method-specific) 10 to 100 times (optimized for each method) the upper end of method's assay range. Use 6% BSA for this solution.

d. Dilute each method-specific conjugate concentrate, in the method's conjugate diluent, to the following dilutions. 1:20 (MMB) or 1:25 (FERR and HCG). Do this for both test and control conjugate concentrates.

e. In a screw top plastic test tube, mix water, hydrated chrome, antigen, and diluted conjugate at the ratios in the immuno-reaction vessel (from the DIMENSION® method parameters for each specific method).

f. In addition, in a screw top plastic test tube, set up the same immuno-reaction mixture, except that 6% BSA is used in place of the antigen solution.

g. Place the test tubes on a rocker and rock the tubes for 2 hours at room temperature.

h. Add 5 μL of the goat anti-mouse coated chrome reagent to each tube and continue rocking for another 2 hours at room temperature.

i. Remove the chrome using magnetic separation and test the supernatants as samples using the appropriate DIMENSION® method, in triplicate. Collect filter data and use the short reads for each method.

j. The total enzymatic activity is defined as the mean result from the tube with no antigen.

k. The enzymatic activity that did not bind chrome is defined as the mean result from the tube with antigen.

l. The total enzymatic activity that is bound to active antibody is the difference between the total and non-binding enzymatic activity.

The results of the testing are summarized in Table 3 below:

TABLE 3

| MMB Lot # | Control % Bound | Test % Bound | Acceptance Criterion | Control Dilution Factor | Test Dilution Factor | Yield Increase (%) |
|---|---|---|---|---|---|---|
| 190141 | 96.8 | 97.2 | Test ≧ Control | 8.4 | 12.1 | 144 |
| 193429 | 94.9 | 95.5 | Test ≧ Control | 9.5 | 16.7 | 176 |
| 195810 | 96.1 | 96.7 | Test ≧ Control | 9.0 | 15.9 | 177 |

| HCG Lot # | Control % Bound | Test % Bound | Acceptance Criterion | Control Dilution Factor | Test Dilution Factor | Yield Increase (%) |
|---|---|---|---|---|---|---|
| 190197 | 52 | 56 | Test ≧ Control | 12.5 | 20 | 160 |
| 193428 | 54 | 66 | Test ≧ Control | 8 | 20 | 250 |
| 195811 | 61 | 76 | Test ≧ Control | 12 | 25 | 208 |

| FERR Lot # | Control % Bound | Test % Bound | Acceptance Criterion | Control Dilution Factor | Test Dilution Factor | Yield Increase (%) |
|---|---|---|---|---|---|---|
| 191009 | 61 | 64 | Test ≧ Control | 12 | 16 | 133 |

The CSA method uses ACMIA immunoassay technology on the DIMENSION® RxL. This method employs competition between antigen (cyclosporine) on chrome particles and antigen in patient samples to determine the amount of cyclosporine in the patient samples. Conjugate that binds the antigen on chrome particles is removed by magnetic separation. The enzymatic activity from conjugate remaining in the supernatant is measured and is directly proportional to the amount of antigen in the patient sample. When an ACMIA assay format is employed, the enzymatic activity observed when testing a sample containing no antigen is indicative of the amount of enzymatic activity that is not bound to active antibody (i.e., cannot bind antigen on chrome). The enzymatic activity observed when no chrome is present is indicative of the total amount of enzymatic activity in the conjugate. These values can be used to estimate the percent of enzymatic activity bound to active antibody.

Results from such a study are shown in Table 4.

TABLE 4

| Lot # | 0 ng/mL Sample mAU | No Chrome mAU | % Not Bound | Acceptance Criterion |
| --- | --- | --- | --- | --- |
| 190104 (Control - Dilution Factor 190) | 151.9 | 1224.6 | 12 | Test ≧ Control |
| 190104A (Test - Dilution Factor 190) | 109.0 | 1165.5 | 9 | |
| 190104 (Control - Dilution Factor 300) | 365.8 | 786.7 | 46 | Test ≧ Control |
| 190104A (Test - Dilution Factor 300) | 280.3 | 760.3 | 37 | |
| 190486(Control - Dilution Factor 190) | 185 | 1728 | 11 | Test ≧ Control |
| 190486A (Test - Dilution Factor 190) | 134 | 1701 | 8 | |
| 190486 (Control - Dilution Factor 300) | 245 | 1233 | 20 | Test ≧ Control |
| 190486A (Test - Dilution Factor 300) | 174 | 1231 | 14 | |
| 194016(Control - Dilution Factor 190) | 161 | 1409 | 11 | Test ≧ Control |
| 194016A (Test - Dilution Factor 190) | 144 | 1479 | 10 | |
| 194016 (Control - Dilution Factor 275) | 90 | 1347 | 7 | Test ≧ Control |
| 194016A (Test - Dilution Factor 275) | 62 | 1309 | 5 | |

It is desirable for conjugates to have high specific activities in the immunoassays for which they are manufactured. The conjugates that were quenched with both NEM and hydrazine (di-deactivated) had higher specific activity than conjugates that were only quenched with NEM.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A conjugate comprising a first polypeptide and a second polypeptide linked together by sulfhydryl groups bound to sulfhydryl receptors wherein sulfhydryl receptors not bound to sulfhydryl groups are in the form of a product of said sulfhydryl receptor and a sulfhydryl receptor deactivation reagent wherein said sulfhydryl receptor deactivation reagent has the formula:

$$R^2HN-(R_1)_n-NHR^2$$

wherein n is 0 or 1, $R^1$ is alkylene of 1 to about 5 carbon atoms and $R^2$ is independently H, alkyl or substituted alkyl.

2. A conjugate according to claim 1 wherein the sulfhydryl receptor deactivation reagent is substantially non-reactive with disulfide linkages when said conjugate comprises disulfide linkages 3. A conjugate according to claim 1 wherein said sulfhydryl receptor deactivation reagent is hydrazine.

4. A conjugate according to claim 1 wherein said polypeptides are independently selected from the group consisting of antibodies and enzymes.

5. A conjugate according to claim 1 wherein said sulfhydryl receptor comprises a 1,2-di-carbonyl substituted olefin, a sulfone substituted olefin, or a carbonyl substituted, halogen substituted carbon atom.

6. A conjugate according to claim 5 wherein said sulfhydryl receptor comprises a 1,2-di-carbonyl substituted olefin that is a maleimide.

7. A conjugate according to claim 5 wherein said sulfhydryl receptor comprises a carbonyl substituted, halogen substituted carbon atom that is a halo-acetyl moiety.

8. A conjugate according to claim 5 wherein said sulfhydryl receptor comprises a sulfone-substituted olefin wherein the olefin bond is conjugated with the sulfone.

9. A conjugate according to claim 1 wherein sulfhydryl groups not bound to sulfhydryl receptors are deactivated.

10. In a method for conjugating a first compound to a second compound wherein said conjugation involves an electrophilic moiety and said method comprises reacting said first compound with said second compound to form a conjugate, the improvement comprising adding a nucleophilic reagent to said conjugate wherein said nucleophilic reagent has the formula $R^2HN-(R_1)_n-NHR^2$, wherein n is 0 or 1, $R_1$ is an alkylene of 1 to about 5 carbon atoms and $R^2$ is independently H, alkyl or substituted alkyl and forms a product upon reaction with unreacted electrophilic moieties of said conjugate wherein said product is the conjugate according to claim 1.

11. A method according to claim 10 wherein said electrophilic moiety comprises a sulfhydryl receptor.

12. A method according to claim 10 wherein said first compound and said second compound are independently selected from the group consisting of enzymes and ligand binders.

13. A method according to claim 12 wherein said ligand binders are polypeptides or polynucleotides.

14. A method according to claim 10 wherein said first compound comprises one or more sulfhydryl groups and said second compound comprises more than one sulfhydryl receptor.

15. A method according to claim 10 wherein said sulfhydryl receptor comprises a carbonyl substituted olefin, a sulfone substituted olefin, or a carbonyl substituted, halogen substituted carbon atom.

16. A method according to claim 10 wherein, when said conjugate comprises disulfide bonds, said nucleophilic reagent is substantially non-reactive with disulfide bonds.

17. A method for conjugating a first polypeptide to a second polypeptide wherein said conjugation involves a sulfhydryl receptor, said method comprising:
(a) combining said first polypeptide with said second polypeptide under conditions for said first polypeptide and said second polypeptide to react to form a conjugate involving said sulfhydryl receptor and
(b) adding a sulfhydryl receptor deactivation reagent having the formula $R^2HN-(R_1)_n-NHR^2$. wherein n is 0 or 1, $R_1$ is an alkylene of 1 to about 5 carbon atoms and $R^2$ is independently H, alkyl or substituted alkyl, to said conjugate wherein said sulfhydryl receptor deactivation reagent forms the conjugate according to claim 1.

18. A method according to claim 17 wherein said first polypeptide and said second polypeptide are independently selected from the group consisting of antibodies and enzymes.

19. A method according to claim 18 wherein said first polypeptide is an enzyme and said second polypeptide is an antibody.

20. A method according to claim 17 wherein said first polypeptide comprises one or more sulfhydryl groups and said second polypeptide comprises more than one sulfhydryl receptor.

21. A method according to claim 17 wherein said sulfhydryl receptor comprises a carbonyl substituted olefin, a sulfone substituted olefin, or a carbonyl substituted, halogen substituted carbon atom.

22. A method according to claim 21 wherein said sulfhydryl receptor comprises a carbonyl substituted olefin that is a 1,2-di-carbonyl substituted olefin.

23. A method according to claim 22 wherein said 1,2-di-carbonyl substituted olefin is a maleimide.

\* \* \* \* \*